United States Patent [19]

Jackman et al.

[11] Patent Number: 5,423,882
[45] Date of Patent: Jun. 13, 1995

[54] CATHETER HAVING ELECTRODE WITH ANNULAR RECESS AND METHOD OF USING SAME

[75] Inventors: Warren M. Jackman, Edmond, Okla.; Wilton W. Webster, Jr., Altadena, Calif.

[73] Assignee: Cordis-Webster, Inc., Baldwin Park, Calif.

[21] Appl. No.: 271,267

[22] Filed: Jul. 6, 1994

Related U.S. Application Data

[63] Continuation of Ser. No. 813,973, Dec. 26, 1991, abandoned.

[51] Int. Cl.6 .............................................. A61N 1/05
[52] U.S. Cl. ..................................... 607/122; 607/126
[58] Field of Search ............... 607/122, 126, 119, 116, 607/115, 137, 138; 128/642

[56] References Cited

U.S. PATENT DOCUMENTS

| | | | |
|---|---|---|---|
| 3,749,100 | 7/1973 | Von Der Mosel | 607/138 |
| 4,135,518 | 1/1979 | Dutcher | 128/419 P |
| 4,325,389 | 4/1982 | Gold | 607/122 |
| 4,437,474 | 3/1984 | Peers-Trevarton | 607/119 |
| 4,760,852 | 8/1988 | Lekholm | 607/116 |
| 5,275,162 | 1/1994 | Edwards et al. | 128/642 |

Primary Examiner—William E. Kamm
Assistant Examiner—Kennedy J. Schaetzle
Attorney, Agent, or Firm—Christie, Parker & Hale

[57] ABSTRACT

A cardiovascular electrode catheter for use in arrhythmia ablation procedures has a dumbbell-shaped large-tip electrode having an annular recess or indentation. The annular recess divides the electrode into a ball-shaped distal portion and a generally cylindrical proximal portion. Both the distal and proximal portions of the electrode have a diameter substantially the same as that of the catheter body. The recess enables the electrode to grip the mitral or tricuspid annulus or the atrial or ventricular myocardial wall to improve ablation procedures.

6 Claims, 5 Drawing Sheets

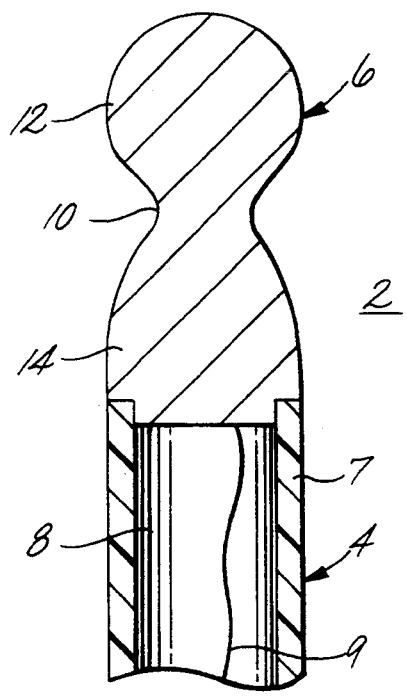
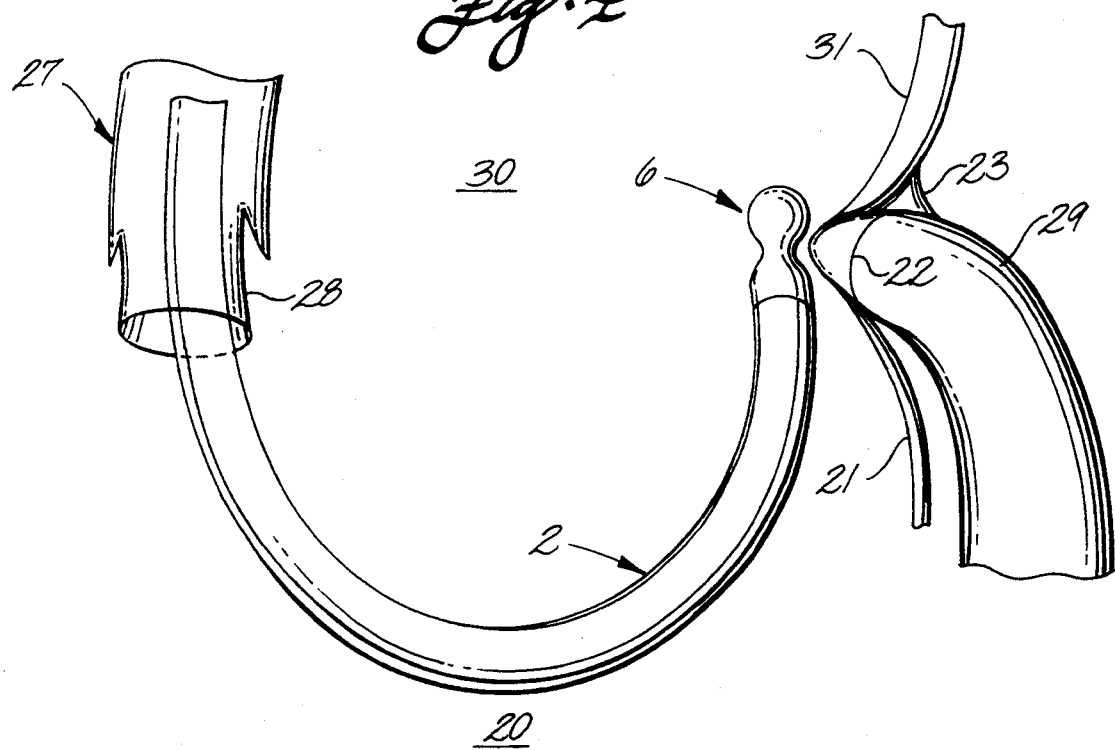

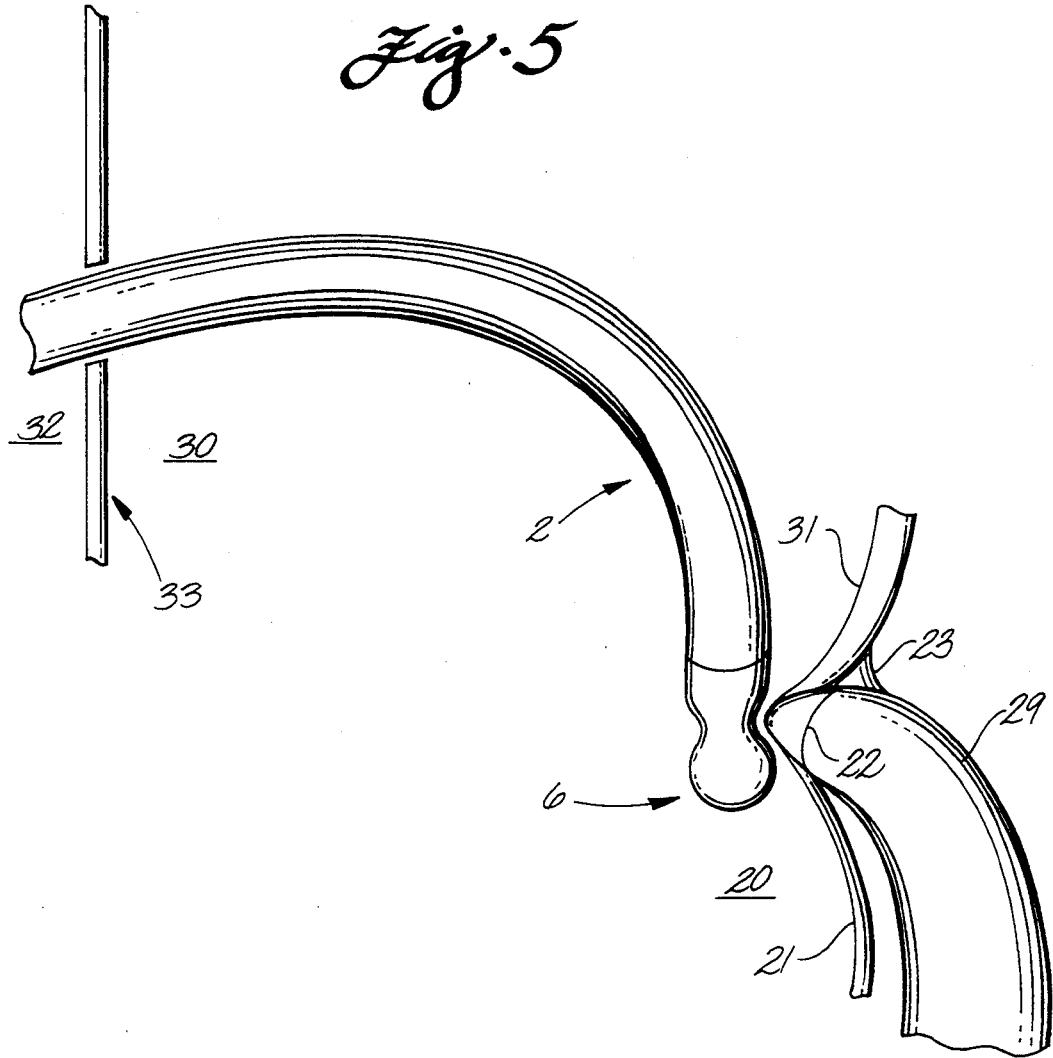

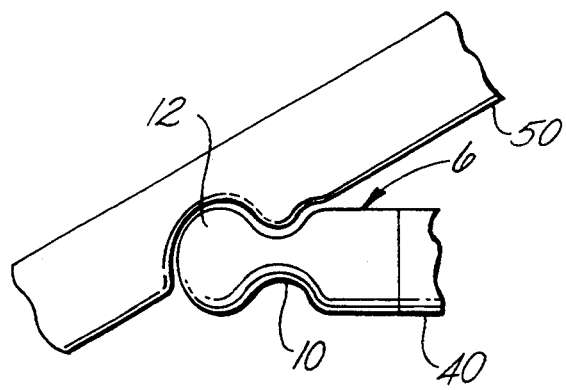
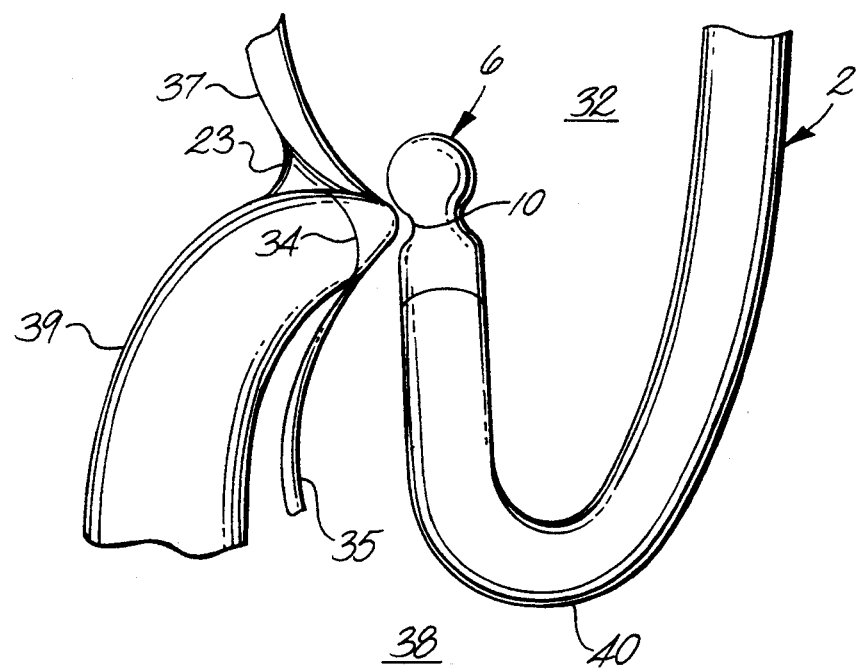

CATHETER HAVING ELECTRODE WITH ANNULAR RECESS AND METHOD OF USING SAME

CROSS-REFERENCE TO RELATED APPLICATION

This is a continuation of Ser. No. 07/813,973, filed Dec. 26, 1991, now abandoned.

FIELD OF THE INVENTION

The present invention relates to electrode catheters and, more particularly, to a catheter having a dumbbell-shaped tip electrode for radio-frequency (RF) catheter ablation of cardiac arrhythmias.

BACKGROUND OF THE INVENTION

Electrode catheters are used to apply RF current (or other forms of electrical energy) within the heart to destroy (ablate) accessory atrioventricular pathways which provide an abnormal electrical connection between the atria and ventricles and produce arrhythmias (heart rhythm disorders). Ablation of the accessory pathway eliminates the arrhythmias.

In such an ablation procedure, the electrode tip of the catheter is brought into and maintained in contact with the endocardium (inner lining of the heart) close to the site of the accessory electrical pathway. When RF current is delivered through the catheter, a small lesion is created by the production of heat due to current passing through the heart tissue, ablating the accessory pathway and a small region of adjacent heart tissue.

In this procedure, the electrode must remain in firm, steady contact with the endocardium. Present catheter electrodes used for electrophysiologic studies of the heart and for ablation procedures in the heart have a generally cylindrical shape with a smooth, rounded distal tip 1, as shown in FIG. 1, or have a smooth, oval-shaped tip 1a, as shown in FIG. 2. Such rounded tip catheters are designed to minimize trauma to the heart. The oval-shaped electrode of FIG. 2 is designed primarily for ablation procedures using high voltage, short duration, direct current shocks, and this shape eliminates the proximate edge of the electrode which otherwise would have a high current density, yet not be in contact with the endocardium. However, both electrode shapes tend to slide along the heart surface. This tendency makes it difficult, in some locations of the heart, such as the mitral annulus and tricuspid annulus, to maintain steady contact between the electrode and the endocardium to adequately deliver the required RF current.

SUMMARY OF THE INVENTION

The present invention provides an electrode catheter having a tip electrode with an annular recess or indentation such that the electrode has a dumbbell shape which helps to maintain contact with the endocardium.

The invention also includes a method of using a catheter having such a dumbbell-shaped tip electrode.

BRIEF DESCRIPTION OF THE DRAWINGS

These and other features and advantages of the present invention will be better understood by reference to the following detailed description when considered in conjunction with the accompanying drawings in which:

FIG. 3 is a side sectional view of the distal end of a cardiovascular electrode catheter having a tip electrode constructed according to the present invention;

FIG. 4 is a side view of an electrode catheter of the present invention in position at the mitral valve annulus of a patient's heart according to one ablation procedure of the invention;

FIG. 5 is a side view of an electrode catheter of the present invention in position at the mitral valve annulus of a patient's heart according to another ablation procedure of the invention;

FIG. 7 is a side view of an electrode catheter of the present invention in position at the tricuspid valve annulus of a patient's heart according to yet another ablation procedure of the invention; and FIG. 8 is a side view of the ball-shaped end of an electrode of the inventive electrode catheter embedded in soft tissue of a wall of a patient's heart.

DETAILED DESCRIPTION

Figure 1:
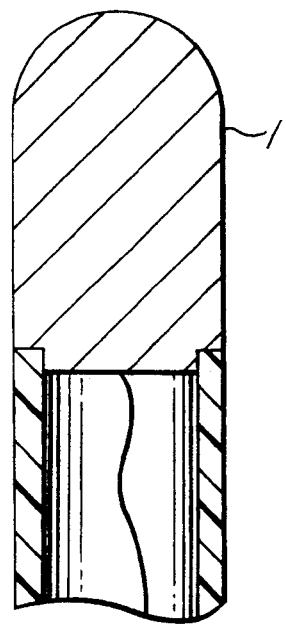
FIG. 1 is a side sectional view of a prior art electrode catheter used in RF catheter ablation procedures.
Figure 2:
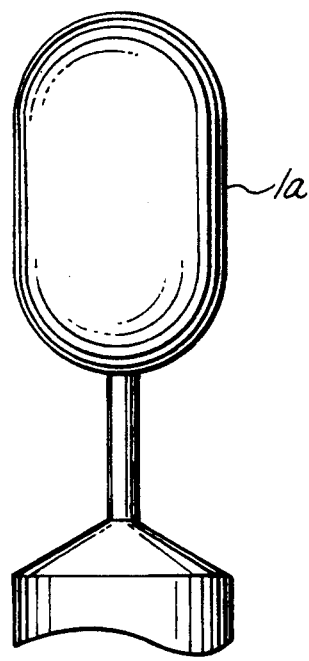
FIG. 2 is a side view of another prior art electrode catheter used in ablation procedures utilizing D.C. shocks.

The distal end of a presently preferred cardiovascular electrode catheter according to the invention is shown in FIG. 3. The catheter 2 comprises a catheter body 4 having an electrode 6 at its tip. The catheter body 4 has a side wall 7, preferably made of flexible and resilient material, and a hollow lumen 8. The electrode 6 is electrically coupled by a wire or wires 9 to an RF current source.

Electrode 6 is dumbbell-shaped, comprising a ball-like distal portion 12, an annular recess or indentation 10, and a generally cylindrical proximal portion 14. Preferably, recess 10 has a smooth, arcuate shape, and the distal portion 12 has a smooth, rounded shape.

It is presently preferred that the diameter of the distal portion 12 is about the same as that of the proximal portion 14 which, in turn, is about the same as the diameter of the catheter body 4. It is understood that the diameters of the distal and proximal portions of the electrode may vary as desired. Preferred diameters range from about 2 mm to about 3 mm. The presently preferred diameter for the distal and proximal portions of the electrode is about 2.33 mm (i.e., about a 7 F size catheter). The diameter at recess 10 is preferably from about 1 mm to about 1.5 mm. The length of the electrode is preferably from about 3 mm to about 6 mm, and most preferably about 4 mm to about 5 mm.

It is particularly preferred the catheter be steerable or deflectable, i.e., that the tip be bendable as desired. Such a steerable feature in combination with the ability to rotate the catheter enables precise placement of the catheter tip within the heart. A presently preferred double-lumen catheter construction which provides a steerable tip is described in U.S. Pat. No. 4,960,134, which is incorporated herein by reference.

FIG. 4 shows the catheter 2 positioned in the heart with the electrode 6 straddling the endocardial surface of the mitral valve (bicuspid valve) annulus 22. In this position, RF current can be applied to the mitral annulus 22 through the electrode to ablate an accessory pathway 23 at that location.

To reach this position, the catheter 2 has been advanced over the mitral valve leaflet 21 to the mitral valve annulus 22 from the cavity of the left ventricle 20. The catheter is placed into an artery (usually a femoral artery), and advanced it to the aorta 27, and then across the aortic valve 28 into the left ventricular cavity 20 which is surrounded by the left ventricular myocardium 29. The catheter is then moved, i.e., withdrawn, until the recess engages the mitral annulus.

It is apparent that the electrode 6 could also be advanced to the mitral annulus 22 from the left atrium 30, if desired, as illustrated in FIG. 5. To reach this position, the catheter 2 is inserted into a vein (usually the right femoral vein), then advanced into the right atrial cavity 32, and then across the interatrial septum 33 (through a patent foramen ovale or by a transeptal puncture procedure) into the left atrial cavity 30, which is surrounded by the left atrial myocardium 31. The catheter is then moved, i.e., withdrawn, until the recess engages the mitral annulus.

Figure 6:
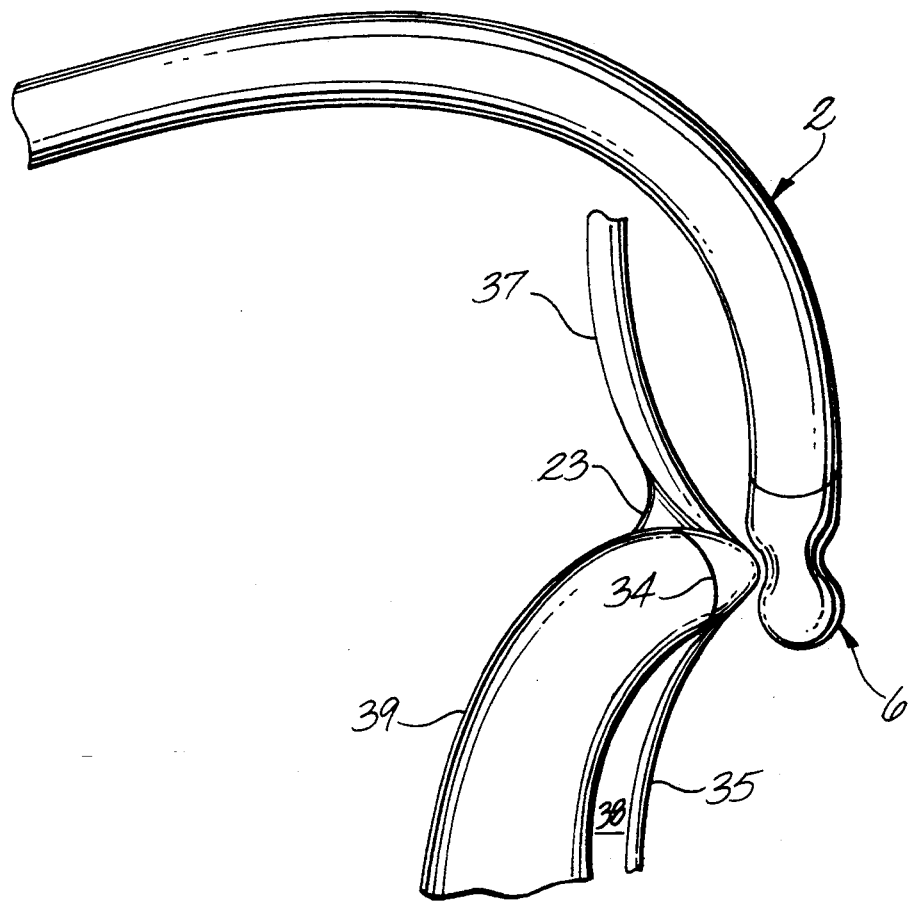
FIG. 6 is a side view of an electrode catheter of the present invention in position at the tricuspid valve annulus of a patient's heart according to another ablation procedure of the invention.

FIG. 6 shows the catheter 2 positioned in the heart with electrode 6 straddling the endocardial surface of the tricuspid valve annulus 34. In this position, RF current can be applied to the tricuspid annulus 34 through the electrode to ablate an accessory pathway 23 at that location. In this depiction, the catheter 2 has been inserted into a vein (usually a femoral, subclavian, or internal jugular vein), then advanced through the inferior vena cava or superior vena cava into the right atrial cavity 32 (which is surrounded by the right atrial myocardium 37), and then positioned against the tricuspid annulus 34, i.e., by withdrawing the catheter.

Electrode 6 can also be positioned firmly against the tricuspid annulus 34, as illustrated in FIG. 7, by curving the end of the catheter about 180°, while still in the right atrial cavity 32, and then advancing the curved portion of the catheter 40 across the tricuspid valve, above the tricuspid valve leaflet 35, into the right ventricular cavity 38 (which is surrounded by the right ventricular myocardium 39) until the annular recess 10 of the electrode 6 engages the tricuspid annulus 34.

With an electrode according to the present invention, the ablation procedure is much simpler and more efficient. To perform ablation, the physician or cardiologist inserts the catheter into an appropriate blood vessel of the patient, and guides it into the heart to the location where the ablation procedure is to take place. For ablating accessory pathways at the mitral valve (for left-sided pathways), the cardiologist slides the catheter tip through the valve orifice from the left ventricle to the left atrium, as shown in FIG. 4, or from the left atrium to the left ventricle, as shown in FIG. 5, and then slowly pulls the tip back until the indentation of the electrode straddles or locks onto the ridge formed at the valve annulus. Directing the catheter through the valve orifice generally requires some degree of flexion in the tip curve mechanism. Once the indentation of the electrode locks onto the ridge formed by the annulus, the tip curve is slowly released to hold the electrode firmly against the annulus.

In the procedure for ablating right-sided pathways by advancing the catheter from the right atrium into the right ventricle, it is preferred, in some patients, to bend or curve the distal end of the catheter back toward the right atrium before the catheter is advanced across the tricuspid valve to allow the indentation on the tip electrode to lock onto the tricuspid annulus, as shown in FIG. 6. The tip curve is then slowly released to hold the electrode firmly against the annulus. In this approach, flexing or increasing the degree of tip curve may hold the electrode firmly against the tricuspid annulus. Once the electrode is locked onto the ridge formed at the mitral or tricuspid valve annulus, the cardiologist delivers energy through the electrode to form a lesion at the ablation site, as is otherwise well known in the art. As used herein, "lesion" means a small area of heart tissue which is killed (necrosis) and is replaced by scar tissue which is electrically inactive.

The large tip "dumbbell" electrode thus enables the electrode to be securely held in the proper place for ablation. The region of the mitral or tricuspid annulus is very useful for ablation of accessory pathways, such as in variations of the Wolff-Parkinson-White syndrome or preexcitation syndrome.

The shape of the present electrode also helps to "grip" the endocardial surface of the heart anywhere in the heart. This is because the ball end indents into the relatively soft tissue 50 of the wall of the heart to help anchor the catheter tip, as shown in the pronounced view of FIG. 8 for purposes of illustration. The present electrode therefore improves ablation of the AV junction, atrial myocardium (to eliminate ectopic atrial tachycardia), AV nodal pathways (to eliminate AV nodal reentrant tachycardia), and ventricular myocardium (to eliminate ventricular tachycardia), in addition to ablation of accessory pathways.

The electrode, according to the invention, further assists the ablation procedure by an increase in dissipation of heat during the application of RF current due to the increased surface area of the electrode exposed to the blood pool. This dissipation of heat helps to maintain a temperature of less than 100° C. at the electrode-tissue interface. When the temperature reaches 100° C., boiling at the endocardial surface occurs which results in an impedance rise which prevents further delivery of energy to the tissue and therefore limits the size of the lesion. By maintaining lower electrode temperatures, a higher voltage can be applied without producing boiling and without an impedance rise, thus resulting in a higher current density deep in the tissue, producing a deeper lesion and an improved likelihood of successful ablation of the accessory pathway.

The preceding description has been presented with reference to a presently preferred embodiment of the invention shown in the drawings. It is apparent that alterations in the described structure can be practiced without meaningfully departing from the scope of this invention.

For example, it is apparent that the depth and width of the annular recess may vary as desired. Moreover, the overall size, i.e., length and diameter of the dumbbell electrode may vary. Additionally, one or more ring electrodes may be provided on the catheter at positions near the tip electrode and spaced apart from the tip electrode. The distal surface of the ball section 12 of the dumbbell electrode may be rounded, as shown in FIG. 3, or may be flat, as desired. The tip electrode is shown in FIG. 3 as being solid throughout. It is apparent that a hollow tip electrode may be used, or that the tip electrode may have a hollow lumen with an open distal end to provide a passageway for withdrawal of blood or other fluid or perfusion of fluid through the catheter. In addition, the shape of the electrode according to the invention may be adaptable for delivering forms of electrical energy other than RF current, e.g., low or high energy D.C. shocks, or other waveforms or frequencies of A.C. electrical current.

Accordingly, the foregoing description should not be read as pertaining only to the precise structure, as described and shown in the accompanying drawings, but rather should be read consistent with and as support to the following claims which have their fullest and fair scope.

What is claimed is:

1. An electrode catheter comprising:
   a catheter body;
   a conductive dumbbell-shaped electrode at the distal end of the catheter body having a proximal end and a distal end separated by a smooth arcuate shaped annular recess; and
   means for electrically connecting the electrode to a source of current, whereby the annular recess is shaped such that it can smoothly engage a heart valve annulus.

2. The catheter of claim 1 wherein the distal end of the electrode is ball shaped.

3. The catheter of claim 2, wherein the diameter of the distal end of the electrode is from about 2 mm to about 3 mm, and the diameter of the annular recess is from about 1 mm to about 1.5 mm.

4. The catheter of claim 3 wherein the diameter of the distal end of the electrode is about 2.3 mm.

5. The catheter of claim 1 wherein the length of the electrode is from about 3 mm to about 6 mm.

6. The catheter of claim 5 wherein the length of the electrode is from about 4 mm to about 5 mm.

* * * * *